(12) United States Patent
Morgan et al.

(10) Patent No.: US 11,364,192 B2
(45) Date of Patent: *Jun. 21, 2022

(54) COMPOSITIONS FOR DENTAL VARNISHES AND METHODS OF MAKING AND USING SAME

(71) Applicant: Colgate-Palmolive Company, New York, NY (US)

(72) Inventors: Andre Morgan, Robbinsville, NJ (US); Sarita Vera Mello, North Brunswick, NJ (US); Marian Georges, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/062,154

(22) PCT Filed: Dec. 18, 2015

(86) PCT No.: PCT/US2015/066583
§ 371 (c)(1),
(2) Date: Jun. 14, 2018

(87) PCT Pub. No.: WO2017/105478
PCT Pub. Date: Jun. 22, 2017

(65) Prior Publication Data
US 2018/0353422 A1    Dec. 13, 2018

(51) Int. Cl.
*A61K 8/92* (2006.01)
*A61K 8/34* (2006.01)
*A61Q 11/00* (2006.01)
*A61K 8/73* (2006.01)
*A61K 8/21* (2006.01)
*A61K 8/04* (2006.01)

(52) U.S. Cl.
CPC .............. *A61K 8/922* (2013.01); *A61K 8/044* (2013.01); *A61K 8/21* (2013.01); *A61K 8/34* (2013.01); *A61K 8/731* (2013.01); *A61K 8/925* (2013.01); *A61K 8/927* (2013.01); *A61Q 11/00* (2013.01); *A61K 2800/30* (2013.01); *A61K 2800/80* (2013.01)

(58) Field of Classification Search
CPC .......... A61K 8/922; A61K 8/31; A61K 8/927; A61K 6/20; A61K 8/34; A61K 8/18; A61K 8/9789; A61K 8/19; A61K 8/21; A61K 8/731; A61K 2800/30; A61Q 11/00
See application file for complete search history.

(56) References Cited

U.S. PATENT DOCUMENTS

| 5,139,768 | A | 8/1992 | Friedman |
| 5,403,577 | A | 4/1995 | Friedman |
| 5,849,266 | A | 12/1998 | Friedman |
| 8,883,212 | B2 | 11/2014 | Pillai et al. |
| 9,833,392 | B2 | 12/2017 | Blanvalet |
| 2007/0189983 | A1 | 8/2007 | Gordon et al. |
| 2009/0142282 | A1* | 6/2009 | Kendall ............... A61Q 11/00 424/52 |
| 2014/0287072 | A1 | 9/2014 | Modak et al. |

FOREIGN PATENT DOCUMENTS

WO    WO 2015/076777    5/2015

OTHER PUBLICATIONS

PCT/US2013/70679, filed Dec. 17, 2012, 18 pages.
"Ethylcellulose (EC) Physical and Chemical Properties A Specialty Polymer With Broad Stability and Compatibility," Aqualon > ethylcellulose (EC) <physical and chemical properties>, Jan. 1, 2002 (Jan. 1, 2002), pp. 1-35, XP55255227. Retrieved from the Internet: URL:http://www.ashland.com//Ashland/Static/Documents/AAFI/PRO 250-42A Aqualon EC.pdf. [retrieved on Mar. 4, 2016) the whole document. US.
International Search Report and Written Opinion for Corresponding Application No. PCT/US2015/066583, dated May 17, 2016. WO.

* cited by examiner

*Primary Examiner* — Lezah Roberts

(57) ABSTRACT

The disclosure describes compositions for dental varnishes, methods of making the compositions, and methods of using the compositions, such as in the treatment and prevention of hypersensitivity in teeth.

13 Claims, No Drawings

COMPOSITIONS FOR DENTAL VARNISHES AND METHODS OF MAKING AND USING SAME

CROSS REFERENCE TO RELATED APPLICATIONS

This application is a national stage entry under 35 U.S.C. § 371 claiming the benefit and priority of PCT/US2015/066583, filed on Dec. 18, 2015.

FIELD

This application is directed to compositions for dental varnishes, methods of making the compositions of dental varnishes, and methods of using the compositions of dental varnishes, such as in the treatment and prevention of hypersensitivity in teeth.

BACKGROUND

Compositions containing fluoride are routinely applied to teeth to aid in the prevention and treatment of a number of dental problems. For example, individuals can apply dentifrices that include fluoride, such as mouthwashes and toothpastes, to their teeth to prevent tooth decay. In these situations, the fluoride may contact the teeth for a relatively limited amount of time, such as a few minutes.

In some cases, it can be desirable to apply fluoride to teeth for a prolonged period of time and to apply an amount of fluoride that is greater than the amount typically found in dentifrices available to consumers. For instance, the prevention and treatment of tooth hypersensitivity and dental caries can be enhanced when fluoride is applied to the teeth for time periods of about or greater than 2 hours. Often, dental varnishes can be used to deliver fluoride directly to the surface of teeth for prolonged periods of time.

Dental varnishes can be applied to teeth using a brush, probe, or other applicator. After the dental varnish dries and any solvents evaporate, a fluoride-containing film is formed on the surface of the teeth that remains on the teeth for a number of hours until the film is removed. In some cases, the dental varnish can be removed by mechanical means, such as the brushing of the teeth or chewing food.

The uniformity of the distribution of the fluoride on the teeth can affect the effectiveness of a dental varnish in the treatment and prevention of tooth problems. Some previous compositions of dental varnishes provide an uneven distribution of fluoride on teeth due to rheological properties of the compositions that cause a non-uniform distribution of fluoride in the dental varnish. In certain instances, the non-uniform distribution of fluoride in previous dental varnishes is caused by rheological properties that result in phase separation of the previous dental varnishes. The rheological properties of dental varnishes can be affected by properties of components of the dental varnishes. For example, in some cases, the properties of the components of the dental varnishes can vary, which results in inconsistent rheological properties of the dental varnish. Thus, the effectiveness of these previous compositions of dental varnishes can also be inconsistent.

There is a need for a dental varnish formulation that provides uniform distribution of fluoride on the teeth.

SUMMARY

Unless otherwise indicated, the terms "%" or "percent" when used in connection with an ingredient of the dental varnish compositions is intended to refer to the percent by wet weight of the indicated ingredient in the dental varnish composition.

In an embodiment, a dental varnish composition can include a fluoride source, such as sodium fluoride. The dental varnish composition can also include a non-aqueous solvent, such as an ethanol. In addition, the dental varnish composition can include ethyl cellulose in an amount effective to achieve suspension of the fluoride source. For example, the dental varnish composition can include ethyl cellulose in an amount from 1% to 10%, from 2% to 8%, or from 3% to 7%. Further, the dental varnish composition can include one or more resins selected from mastic, colophonium, or a combination thereof. In some cases, the dental varnish composition can have a high shear viscosity that is at least 1,500 centipoise (cps). In an additional example, the dental varnish composition can have a high shear viscosity from 1,500 cps to 6,500 cps.

In another embodiment, a dental varnish composition can include a non-aqueous solvent, such as ethanol present in an amount from 20% to 38%. The dental varnish composition can also include a fluoride source present in an amount from 1% to 10%. Additionally, the dental varnish composition can include ethyl cellulose in an amount effective to achieve suspension of the fluoride source. The ethyl cellulose can have a viscosity no greater than 45 centipoise (cps). Further, the dental varnish composition can include one or more resins selected from mastic, colophonium, or a combination thereof. The mastic can be present in an amount from 18% to 36% and the colophonium can be present in an amount from 25% to 40%.

In an additional embodiment, a process can include combining a first portion of an amount of an ethanol solution and a first portion of an amount of colophonium to form an ethanol solution and colophonium mixture. The process can also include combining the ethanol solution and colophonium mixture with a fluoride source to form a first dental varnish component. Additionally, the process can include combining a second portion of the amount of the ethanol solution, a second portion of the amount of the colophonium, a mastic, and an ethyl cellulose to form a second dental varnish component. Further, the process can include combining the first dental varnish component, the second dental varnish component, and a remainder of the amount of the ethanol solution to produce a composition of a dental varnish.

DETAILED DESCRIPTION

This disclosure is directed to compositions for dental varnishes, methods of making dental varnishes, and methods of using dental varnishes. The compositions described herein have rheological properties that can decrease or eliminate instances of phase separation in dental varnishes. In particular, the compositions of dental varnishes described herein can include components that provide consistent rheological properties that cause a substantially uniform distribution of fluoride throughout the dental varnish. Accordingly, when the dental varnish is applied to teeth, the fluoride is distributed evenly on the teeth and provides effective treatment and/or prevention of dental problems. Finally, the dental varnish of the present disclosure provides an improved appearance on the tooth surface.

In an embodiment, compositions of dental varnish can include ethyl cellulose to provide rheological properties of the dental varnish that minimize or eliminate phase separation of the dental varnish. The rheological properties of dental varnish compositions that include ethyl cellulose can also provide a substantially uniform distribution of fluoride in the dental varnish. In some cases, the ethyl cellulose can be a replacement for shellacs that have been included in previous compositions of dental varnishes. The use of a synthetic component in dental varnishes, such as ethyl cellulose, in lieu of a natural component, such as shellac, can provide improved control over rheological properties, in particular, the ethyl cellulose can provide rheological properties of dental varnishes that are improved over compositions of dental varnishes that include a shellac or a shellac-containing wax. For example, the instances of phase separation for the dental varnish can decrease when ethyl cellulose is used in compositions of dental varnishes as opposed to a shellac or a shellac-containing wax. Furthermore, the adhesive properties of the dental varnish compositions including ethyl cellulose and the suspension of fluoride in the dental varnish compositions are at least comparable to the previous dental varnishes that include shellac and/or a wax containing shellac.

Ethyl cellulose is an ether derivative of cellulose. Cellulose is a natural polysaccharide made up of long chains of β anhydroglucose units joined together by acetal linkages. Each anhydroglucose unit has three hydroxyl groups, which may form ethyl ethers, e.g., by the reaction of ethyl chloride with alkali cellulose, thus providing ethyl cellulose. The degree of ethoxylation varies in different ethyl cellulose products. Complete substitution of all three groups on the anhydroglucose units would give the triethyl ether possessing a substitution value of 3, or 54.88% ethoxyl. The completely substituted triethylcellulose, however, lacks strength and flexibility, is not thermoplastic, and exhibits limited compatibility and solubility. The degree of substitution, as well as the molecular weight, affects the viscosity and solubility of the product. In certain embodiments, the ethyl cellulose has an average substitution value of between 2.25 and 2.60 ethoxyl groups per anhydroglucose unit, or 44% to 52% ethoxyl content. In some cases, the ethyl cellulose has an average substitution value of 2.46-2.58 ethoxyl groups per anhydroglucose unit, corresponding to an ethoxyl content of 48% to 49.5%.

In an embodiment, compositions of dental varnishes can include at least 1% ethyl cellulose, at least 2% ethyl cellulose, at least 3% ethyl cellulose, or at least 4% ethyl cellulose. Additionally, compositions of dental varnishes can include no greater than 9% ethyl cellulose, no greater than 8% ethyl cellulose, no greater than 7% ethyl cellulose, or no greater than 6% ethyl cellulose. In an illustrative example, compositions of dental varnishes can include from 1% to 10% ethyl cellulose. In another illustrative example, compositions of dental varnishes can include from 2% to 8% ethyl cellulose. In an additional illustrative example, compositions of dental varnishes can include from 3% to 7% ethyl cellulose. In other illustrative examples, compositions of dental varnishes can include from 2% to 3% ethyl cellulose, from 2% to 4% ethyl cellulose, from 5% to 7% ethyl cellulose, or from 4% to 6% ethyl cellulose.

Ethyl cellulose included in compositions of dental varnishes can have a viscosity of at least 5 centipoise (cps), at least 15 cps, at least 25 cps, at least 35 cps, at least 45 cps, or at least 55 cps. Additionally, ethyl cellulose included in compositions of dental varnishes can have a viscosity of no greater than 125 cps, no greater than 115 cps, no greater than 105 cps, no greater than 95 cps, no greater than 85 cps, no greater than 75 cps, or no greater than 65 cps. In an illustrative example, ethyl cellulose included in compositions of dental varnishes can have a viscosity from 5 cps to 125 cps, from 20 cps to 110 cps, from 30 cps to 100 cps, from 40 cps to 90 cps, or from 80 cps to 105 cps. In an additional illustrative example, ethyl cellulose included in compositions of dental varnishes can have a viscosity from 5 cps to 60 cps, from 7 cps to 50 cps, from 8 cps to 45 cps, from 10 cps to 30 cps, or from 20 cps to 55 cps. In some cases, the viscosity of the ethyl cellulose can be related to a molecular weight of the ethyl cellulose. Furthermore, unless noted otherwise, "viscosity" as used herein refers to dynamic viscosity, sometimes referred to as shear viscosity.

In a particular example, ethyl cellulose included in compositions of dental varnishes can have a viscosity of at least 6 cps, at least 7 cps, or at least 8 cps. In addition, ethyl cellulose included in compositions of dental varnishes can have a viscosity no greater than 12 cps, no greater than 11 cps, no greater than 10 cps, or no greater than 9 cps. In an illustrative example, ethyl cellulose included in compositions of dental varnishes can have a viscosity from 5 cps to 13 cps, from 6 cps to 12 cps, from 7 cps to 11 cps, or from 8 cps to 10 cps.

In other cases, ethyl cellulose included in compositions of dental varnishes can have a viscosity of at least 16 cps, at least 17 cps, at least 18 cps, or at least 19 cps. Further, ethyl cellulose included in compositions of dental varnishes can have a viscosity that is no greater than 24 cps, no greater than 23 cps, no greater than 22 cps, no greater than 21 cps, or no greater than 20 cps. In an illustrative example, ethyl cellulose included in compositions of dental varnishes can have a viscosity from 15 cps to 25 cps, from 16 cps to 26 cps, from 17 cps to 25 cps, or from 18 cps to 24 cps.

Also, ethyl cellulose included in compositions of dental varnishes can have a viscosity of at least 38 cps, at least 40 cps, at least 42 cps, at least 44 cps, or at least 46 cps. Additionally, ethyl cellulose included in compositions of dental varnishes can have a viscosity no greater than 56 cps, no greater than 54 cps, no greater than 52 cps, no greater than 50 cps, or no greater than 48 cps. In an illustrative example, ethyl cellulose included in compositions of dental varnishes can have a viscosity from 35 cps to 60 cps, from 35 cps to 48 cps, from 40 cps to 55 cps, or from 44 cps to 52 cps.

In some instances, the amount of ethyl cellulose included in dental varnish compositions can be related to a viscosity of the ethyl cellulose included in the dental varnish. For example, an ethyl cellulose having a viscosity from 7 cps to 12 cps can be present in compositions of dental varnishes in an amount from 3% to 8% or from 4% to 7%. In another example, an ethyl cellulose having a viscosity from 17 cps to 25 cps can be present in compositions of dental varnishes in amount from 1% to 5% or from 2% to 4%. In an additional example, an ethyl cellulose having a viscosity from 45 cps to 55 cps can be present in compositions of dental varnishes in an amount from 1% to 5% for from 2% to 3%.

The viscosity of the ethyl cellulose included in compositions of dental varnishes can be measured according to the ASTM D 914 standard as of the time of filing this application using 5% by weight ethyl cellulose in a solution of an 80:20 toluene ethanol mixture by weight on a sample dried 30 minutes at 100° C.

Dental varnish compositions can also include a non-aqueous solvent. For example, compositions of dental varnishes can include ethanol, ethyl acetate, or combinations thereof, in a particular example, compositions of dental varnishes can include at least 20% of a non-aqueous solvent, at least 22% of the non-aqueous solvent, at least 24% of the non-aqueous solvent, or at least 26% of the non-aqueous solvent. Additionally, compositions of dental varnishes can include no greater than 38% of the non-aqueous solvent, no greater than 36% of the non-aqueous solvent, no greater than 34% of the non-aqueous solvent, or no greater than 32% of the non-aqueous solvent. In illustrative examples, compositions of dental varnishes can include from 20% to 38% of the non-aqueous solvent, from 22% to 32% of the non-aqueous solvent, from 24% to 30% of the non-aqueous solvent, from 25% to 29% of the non-aqueous solvent, or from 23% to 26% of the non-aqueous solvent. In a particular illustrative example, the non-aqueous solvent can include ethanol.

In some cases, dental varnishes can include ethanol derived from an ethanol solution, such as a 96% ethanol solution having a balance of other components including water. Compositions of dental varnishes can have no greater than 2% water, no greater than 1% water, or be substantially free of water. As used herein, the term "substantially free" with respect to a material is meant to indicate that the substance includes at most trace amounts of the material.

Compositions of dental varnishes can include one or more resins. As used herein, the term "resin" can refer to a natural resin that is secreted or extracted from a plant or tree and/or a synthetic resin including an artificial polymer base. The one or more resins included in compositions of dental varnishes can include natural resins, such as a mastic, colophonium, or both. Mastic can include a resin obtained from the mastic tree (*Pistacia lentiscus*) and colophonium can include a resin derived from the stumps or sap of various plants, e.g. certain pine and conifer species.

A total amount of one or more resins included in dental varnish compositions can be at least 45%, at least 47%, at least 49%, at least 51%, at least 53%, or at least 55%. Also, a total amount of one or more resins included in dental varnish compositions can be no greater than 69%, no greater than 67%, no greater than 65%, no greater than 63%, no greater than 61%, or no greater than 59%. In an illustrative example, a total amount of one or more resins included in compositions of dental varnishes can be from 42% to 70%, from 50% to 65%, from 56% to 62%, or from 59% to 61%.

In particular implementations, compositions of dental varnishes can include at least 25% of a first resin, at least 27% of the first resin, at least 29% of the first resin, or at least 31% of the first resin. Further, compositions of dental varnishes can include no greater than 39% of the first resin, no greater than 37% of the first resin, no greater than 35% of the first resin, or no greater than 33% of the first resin. In illustrative examples, compositions of dental varnishes can include from 25% to 40% of the first resin, from 27% to 37% of the first resin, from 29% of the first resin to 35% of the first resin, or from 31% of the first resin to 33% c of the first resin. The first resin can include colophonium. The colophonium included in compositions of dental varnishes can be compendial grade colophonium.

Additionally, compositions of dental varnishes can include at least 19% of a second resin, at least 21% of the second resin, at least 23% of the second resin, or at least 25% of the second resin. Compositions of dental varnishes can also include no greater than 35% of the second resin, no greater than 33% of the second resin, no greater than 31% of the second resin, or no greater than 29% of the second resin, in illustrative examples, compositions of dental varnishes can include from 18% to 36% of the second resin, from 24% to 32% of the second resin, from 26% to 30% of the second resin, or from 27% to 29% of the second resin. The second resin can include a mastic. The mastic included in compositions of dental varnishes can be compendial grade mastic.

In situations where compositions of dental varnishes include colophonium and a mastic, the dental varnish compositions can include from 28% to 38% colophonium and from 22% to 32% mastic. In an additional example, dental varnish compositions can include 30% to 35% colophonium and from 24% to 30% mastic. In another example, dental varnish compositions can include from 32% to 34% colophonium and from 26% to 28% mastic.

Compositions of dental varnishes can also include a fluoride source. The fluoride source can include a fluorine-containing compound that has a beneficial effect on the care and hygiene of the teeth, e.g. diminution of enamel solubility in acid and protection of the teeth against decay. The fluoride source can include soluble salts of a fluorine anion; such as, for example: sodium fluoride, potassium fluoride, calcium fluoride, zinc fluoride, zinc ammonium fluoride, lithium fluoride, ammonium fluoride, stannous fluoride, stannous fluorozirconate. The fluoride source can also include complex fluorides, monofluorophosphates and salts thereof such as, for example, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides.

The fluoride source can be present in compositions of dental varnishes in an amount of at least 5,000 parts per million (ppm), at least 7,000 ppm, at least 10,000 ppm, at least 12,000 ppm, at least 15,000 ppm, or at least 18,000 ppm. Additionally, the fluoride source can be present in compositions of dental varnishes in an amount no greater than 30,000 ppm, no greater than 28,000 ppm, no greater than 25,000 ppm, or no greater than 23,000 ppm. In an illustrative example, compositions of dental varnishes can include 5,000 ppm to 30,000 ppm of a fluoride source, 10,000 ppm to 25,000 ppm of a fluoride source, 16,000 ppm to 24,000 ppm of a fluoride source, or 21,000 ppm to 23,000 ppm of a fluoride source.

In order to provide a concentration of the fluoride source in a specified ppm range, the exact weight percentage of the fluoride source in the compositions may vary, depending upon the stoichiometric properties of different fluoride sources. In some cases, compositions of dental varnishes can include at least 1% of a fluoride source, at least 2% of a fluoride source, at least 3% of a fluoride source, or at least 4% of a fluoride source. Further, compositions of dental varnishes can include no greater than 9% of a fluoride source, no greater than 8% of a fluoride source, no greater than 7% of a fluoride source, or no greater than 6% of a fluorides source. In an illustrative example, compositions of dental varnishes can include from 1% to 10% of a fluoride source, from 2% to 8% of a fluoride source, from 3% to 7% of a fluoride source, or from 4% to 6% of a fluoride source. The amount of the fluoride source included in compositions of dental varnishes can be at least the amount of ethyl cellulose in the compositions of dental varnishes. Alternatively, the amount of the fluoride source included in compositions of dental varnishes can be less than the amount of ethyl cellulose in the compositions of dental varnishes. In a particular implementation, the fluoride source is sodium fluoride.

Compositions of dental varnishes can include one or more additional components, such as one or more waxes, one or more flavoring components, one or more sweetener components, one or more coloring components, or combinations thereof. The one or more sweetener components can include sucrose, lactose, maltose, xylitol, sodium cyclamate, perillartine, AMP (aspartyl phenyl alanine methyl ester), saccharin, combinations thereof, and the like. The one or more flavoring components can include flavoring oils, such as oil of spearmint, oil of peppermint, oil of wintergreen, oil of clove, oil of sage, oil of eucalyptus, oil of marjoram, oil of cinnamon, oil of lemon, oil of raspberry, oil of orange, combinations thereof, and the like.

Dental varnish compositions can include a wax in an amount of at least 1%, at least 2%, or at least 3%. In addition, the compositions of dental varnish can also include a wax present in amount of no greater than 6%, no greater than 5%, or no greater than 4%. In an illustrative example, the compositions of dental varnish can include wax present in an amount from 1% to 6%, from 2% to 5%, or from 3% to 4%. In some cases, the wax can include a beeswax, such as white beeswax. The white beeswax can be United States Pharmaceutical (USP) grade. Additionally, the compositions of dental varnishes may be free from a wax including shellac.

Further, compositions of dental varnishes can include no greater than 3% of one or more sweetener components, no greater than 2% of one or more sweetener components, or no greater than 1% of one or more sweetener components. In an illustrative example, the compositions of dental varnishes can include from 0.4% to 0.9% of one or more sweetener components. In some cases, a sweetener component can include a saccharin, such as saccharin 550. Compositions of dental varnishes can include no greater than 3% of one or more flavoring components, no greater than 2% of one or more flavoring components, or no greater than 1% of one or more flavoring components. In another illustrative example, the compositions of dental varnishes can include from 0.4% to 0.9% of one or more flavoring components.

Other materials may be incorporated in the compositions of dental varnishes, such as whitening agents (e.g., urea peroxide, calcium peroxide, titanium dioxide, hydrogen peroxide, complexes of polyvinylpyrrolidone (PVP) and hydrogen peroxide), preservatives, vitamins (e.g., vitamin B6, vitamin B12, vitamin E, vitamin K), silicones, chlorophyll compounds, potassium salts (e.g., potassium nitrate) for the treatment of dental hypersensitivity, anti-tartar agents (e.g., sodium tripolyphosphate and di- and tetra-alkali metal pyrophosphate salts such as di- and tetrasodium pyrophosphate), calcium-based salts (e.g., dicalcium phosphate, tricalcium phosphate, precipitated calcium carbonate to be used alone or in combination with amino acids such as L-arginine), or combinations thereof. These additional materials can be present in compositions of dental varnishes in amounts that do not adversely affect the rheological properties of the dental varnishes and/or the effectiveness of the dental varnishes in the treatment or prevention of tooth problems, such as amounts no greater than 5%, no greater than 4%, no greater than 3%, no greater than 2%, or no greater than 1%.

In one embodiment, the dental varnish according to the invention can have a high shear viscosity of at least 700 cps, at least 900 cps, at least 1100 cps, at least 1,000 cps, at least 2,000 cps, at least 2,500 cps, at least 3,000 cps, at least 3,500 cps, or at least 4,000 cps, and can have a high shear viscosity of no greater than 8,000 cps, no greater than 7,000 cps, no greater than 6,500 cps, no greater than 6,000 cps, no greater than 5,500 cps, or no greater than 5,000 cps. In an illustrative example, compositions of dental varnish according to the invention can have a high shear viscosity from 600 cps to 8,500 cps, from 1,500 cps to 6,500 cps, from 2,500 cps to 5,500 cps, or from 3,000 cps to 4,000 cps. In some cases, compositions of dental varnish according to the invention can have a high shear viscosity from 5,000 cps to 6,000 cps.

The high shear viscosity can be measured using a HA, RV, or LV Brookfield DV* series or DV*T series viscometer having a v72, v73, or v74 spindle at a shear rate of 1 rotation per minute (RPM). The majority of data points measured can be measured between 10% torque and 100% torque.

Furthermore, compositions of dental varnishes can have a yield stress as the shear rate is ramping up from 8 Pascals (Pa) to 45 Pa, from 18 Pa to 40 Pa, from 24 Pa to 38 Pa, from 28 Pa to 36 Pa, or from 31 Pa to 35 Pa. Also, compositions of dental varnishes can have a yield stress as the shear rate is ramping down from 1 Pa to 15 Pa, from 4 Pa to 14 Pa, from 8 Pa to 13 Pa, or from 10 Pa to 12 Pa. Compositions of dental varnishes can have a ratio of yield stress when a shear rate is ramping up to a yield stress when a shear rate is ramping down of at least 3, at least 4, at least 5, at least 6, or at least 7. The ratio of yield stress when a shear rate is ramping up to yield stress when a shear rate is ramping down can be no greater than 11, no greater than 10, no greater than 9, or no greater than 8. In an illustrative example, the ratio of yield stress when a shear rate is ramping up to yield stress when a shear rate is ramping down can be between 3 and 8. In another illustrative example, the ratio of yield stress when a shear rate is ramping up to yield stress when a shear rate is ramping down can be between 2 and 5. In a further illustrative example the ratio of yield stress when a shear rate is ramping up to yield stress when a shear rate is ramping down can be between 2.5 and 3.5.

The yield stress can be measured using a HA, RV, or LV Brookfield DV* series or Brookfield DV*T series viscometer having a v72, v73, or v74 spindle with a minimum shear rate of 0.5 RPM and a maximum shear rate of 200 RPM.

Compositions of dental varnishes according to embodiments described herein can have a release of fluoride of 0.2 mg to 0.7 mg per g of dental varnish after 4 hours or a release of fluoride of 0.4 mg to 0.6 mg per g of dental varnish after 4 hours. In addition, compositions of dental varnishes can have a release of fluoride of 0.6 mg to 1.2 mg per g of dental varnish after 24 hours or a release of fluoride of 0.7 mg to 1.1 mg per g of dental varnish after 24 hours. The release of fluoride can be measured based on dental varnishes placed on bovine enamel.

Furthermore, dental varnishes can have an uptake of fluoride on bovine enamel of 2500 ppm to 4500 ppm or 3000 ppm to 400 ppm. The fluoride uptake can be measured according to test method 40 of the Food and Drug Administration (FDA) Monograph or a variation of the test method 40 of the FDA Monograph.

Also, dental varnishes can have a retention from 50% to 95% on bovine enamel after 1 hour or a retention from 60% to 90% on bovine enamel after 1 hour. In some instances, dental varnishes can have a retention after 4 hours from 40% to 80% on bovine enamel or from 50% to 75% on bovine enamel. Additionally, dental varnishes described herein can have a retention after 24 hours from 40% to 70% on bovine enamel or a retention after 24 hours from 45% to 65% on bovine enamel.

In some cases, when dental varnishes having compositions described herein are applied to tooth enamel, the dental varnishes can be free of color and appear to be clear. That is, very little, if any, light is absorbed by the dental varnish. In this way, the compositions of dental varnishes described herein differ from some previous compositions because the previous compositions have a yellow color. That is, the previous compositions of dental varnishes absorb wavelengths of electromagnetic radiation from 570 nm to 590 nm.

In a particular illustrative example, compositions of dental varnishes can have from 32% to 34% colophonium, from 26% to 29% ethanol, from 26% to 29% mastic, from 4% to 6% sodium fluoride, and from 2% to 4% ethyl cellulose. In these compositions, the viscosity of the ethyl cellulose can be from 18 cps to 24 cps. Additionally, these compositions can include from 2% to 4% white beeswax, from 0.4% to 0.9% saccharin 550, and from 0.4% to 0.9% of a flavoring component (such as Raspberry Flavor). Furthermore, these compositions of dental varnishes can have a viscosity from 3,700 cps to 3,900 cps and a ratio of yield stress as the shear rate is ramping up to yield stress when a shear rate is ramping down from 2.5 to 3.5.

In another particular illustrative example, compositions of dental varnishes can have from 32% to 34% colophonium, from 27% to 29% ethanol, from 26% to 29% mastic, from 4% to 6% sodium fluoride, and from 2% to 3% ethyl cellulose. In these compositions, the viscosity of the ethyl cellulose can be from 40 cps to 52 cps. Additionally, these compositions can include from 2% to 4% white beeswax, from 0.4% to 0.9% saccharin 550, and from 0.4% to 0.9% of a flavoring component (such as Raspberry Flavor). Furthermore, these compositions of dental varnishes can have a viscosity from 3,100 cps to 3,300 cps and a ratio of yield stress as the shear rate is ramping up to yield stress when a shear rate is ramping down from 6 to 8.

In a further particular illustrative example, compositions of dental varnishes can have from 32% to 34% colophonium, from 23% to 26% ethanol, from 26% to 29% mastic, from 4% to 6% sodium fluoride, and from 5% to 7% ethyl cellulose. In these compositions, the viscosity of the ethyl cellulose can be from 8 cps to 11 cps. Additionally, these compositions can include from 2% to 4% white beeswax, from 0.4% to 0.9% saccharin 550, and from 0.4% to 0.9% of a flavoring component (such as Raspberry Flavor). Furthermore, these compositions of dental varnishes can have a viscosity from 5,400 cps to 5,600 cps and a ratio of yield stress as the shear rate is ramping up to yield stress when a shear rate is ramping down from 2.5 to 3.5.

In an additional illustrative example, compositions of dental varnishes can have from 31% to 33% colophonium, from 25% to 28% ethanol, from 28% to 31% mastic, from 4% to 6% sodium fluoride, and from 1% to 4% ethyl cellulose. In these compositions, the viscosity of the ethyl cellulose can be from 80 cps to 105 cps. These compositions can also include from 2% to 4% white beeswax, from 0.4% to 0.9% saccharin, and from 0.4% to 0.9% of a flavoring component (such as Raspberry Flavor). In addition, these compositions of dental varnishes can have a viscosity from 1,200 cps to 1,600 cps and a ratio of yield stress as the shear rate is ramping up to yield stress when a shear rate is ramping down from 4 to 6.

The compositions of dental varnishes described herein can be utilized in the prevention and/or treatment of dental problems. For example, compositions of dental varnishes can be used to prevent and/or treat tooth hypersensitivity in humans, domesticated animals, or both. As used herein, the term "domesticated animal" includes animals generally recognized to be pets, for example dogs and cats. In another example, the compositions of dental varnishes can be used to prevent dental carries in humans, domesticated animals, or both. In an illustrative example, a method of prevention and/or treatment of dental problems can include applying a composition of a dental varnish to the surface of one or more teeth. The dental varnish composition can be applied using a brush, spray, or another applicator. In some cases, an amount of dental varnish applied to the one or more teeth can be from 0.005 g to 0.03 grams, from 0.009 g to 0.025 g, or from 0.01 g to 0.02 g. In an illustrative example, at least 0.02 g of a dental varnish composition can be applied to the one or more teeth. In addition, the compositions of dental varnishes can be in contact with the one or more teeth for a duration of at least 1 hour, at least 2 hours, at least 3 hours, at least 4 hours, at least 5 hours or at least 6 hours. Furthermore, the compositions of dental varnishes can be in contact with the one or more teeth for a duration no greater than 24 hours, no greater than 20 hours, no greater than 16 hours, or no greater than 12 hours. In some instances, the compositions of dental varnishes can be in contact with the one or more teeth for a duration from 30 minutes to 10 hours, from 1 hour to 9 hours, or from 2 hours to 6 hours.

An example process to make a dental varnish according to embodiments described herein includes combining a first portion of an amount of ethanol solution and a first portion of an amount of colophonium. In some cases, the ethanol solution can be a 96% ethanol solution. In addition, the first portion of the amount of ethanol solution and the first portion of the amount of colophonium can be mixed for a period of time sufficient to disperse the colophonium in the ethanol solution. The mixing can take place via mechanical means. Further, the first portion of the ethanol solution and the first portion of the colophonium solution can be covered while being mixed.

An amount of ethanol solution can include from 50% to 75% by weight of a total weight of the ethanol solution and colophonium mixture and an amount of the colophonium can include from 25% to 45% by weight of a total weight of the ethanol solution and colophonium mixture. Additionally, an amount of ethanol solution can include from 60% to 70% by weight of a total weight of the ethanol solution and colophonium mixture and an amount of the colophonium can include from 30% to 40% by weight of a total weigh of the ethanol solution and colophonium mixture.

Additionally, the ethanol solution and colophonium mixture can be combined with a fluoride source to form a first dental varnish component. For example, the ethanol solution and colophonium mixture can be combined with sodium fluoride. In particular, the ethanol solution and colophonium mixture can be mixed with the fluoride source for a specified duration, such as from 15 minutes to 60 minutes, from 20 minutes to 50 minutes, or from 25 minutes to 35 minutes. Additionally, the colophonium/ethanal solution mixture and the fluoride source can be covered while being mixed. In some cases, the first dental varnish component is to be set aside for a period of time before being used again during the process 100, such as from 15 minutes to 50 minutes, from 25 minutes to 45 minutes, or from 30 minutes to 40 minutes.

The first dental varnish component can include an amount of the ethanol solution and colophonium mixture from 50% to 75% by weight of a total weight of the first dental varnish component and an amount of the fluoride source can include from 25% to 45% by weight of a total weight of the first dental varnish component. Further, the first dental varnish component can include an amount of the ethanol solution and colophonium mixture from 60% to 70% by weight of a total weight of the first dental varnish component and an amount of the fluoride source can include from 30% to 40% by weight of a total weight of the first dental varnish component.

Furthermore, a second portion of the amount of the ethanol, a second portion of the amount of the colophonium, mastic, and ethyl cellulose can be combined to form a second dental varnish component. In one example, the ethyl cellulose can have a viscosity from 8 cps to 12 cps. In another example, the ethyl cellulose can have a viscosity from 18 cps to 24 cps. In an additional example, the ethyl cellulose can have a viscosity from 40 cps to 52 cps. The second portion of the amount of the ethanol, the second portion of the amount of the colophonium, the mastic, and the ethyl cellulose can be mixed for a duration, such as from 1 hour to 6 hours, from 2 hours to 5 hours, or from 3 hours to 4 hours. Additionally, the second portion of the amount of the ethanol, the second portion of the amount of the colophonium, the mastic, and the ethyl cellulose can be mixed at a temperature from 100° C. to 125° C., from 105° C. to 120° C., or from 110° C. to 118° C. In some cases, the second portion of the amount of the ethanol, the second portion of the amount of the colophonium, the mastic, and the ethyl cellulose can be mixed under reflux. Optionally, an additional amount of the ethanol solution can be added after mixing the second portion of the amount of the ethanol solution, the second portion of the amount of the colophonium, the mastic, and the ethyl cellulose.

The second dental varnish component can include a second portion of the amount of ethanol from 18% to 35% by weight of a total weight of the second dental varnish component or the second dental varnish component can include a second portion of the amount of ethanol from 22% to 28% by weight of a total weight of the second dental varnish component. In addition, the second dental varnish component can include a second portion of the amount of colophonium from 20% to 45% by weight of a total weight of the second dental varnish component or the second dental varnish component can include a second portion of the amount of colophonium from 30% to 40% by weight of a total weight of the second dental varnish component. Further, the second dental varnish component can include mastic from 20% to 45% by weight of a total weight of the second dental varnish component or the second dental varnish component can include mastic from 25% to 37% by weight of a total weight of the second dental varnish component. Also, the second dental varnish component can include ethyl cellulose from 1% to 10% by weight of a total weight of the second dental varnish component, from 1.5% to 8% by weight of a total weight of the second dental varnish component, from 2% to 7% by weight of a total weight of the second dental varnish, or from 2.5% to 6% by weight of a total weight of the second dental varnish component. The second dental varnish component can also include wax, such as a white wax, from 2% to 5% by weight of a total weight of the second dental varnish component. Additionally, the second dental varnish component can include a sweetener component, such as saccharin, from 0.5% to 1.5% by weight of a total weight of the second dental varnish component. In an illustrative example, the second dental varnish component can include the second portion of the amount of ethanol from 20% to 30% by weight of a total weight of the second dental varnish component, the second amount of the colophonium from 30% to 40% by weight of a total weight of the second dental varnish component, mastic from 27% to 35% by weight of a total weight of the second varnish component, ethyl cellulose from 2% to 6% by weight of a total weight of the second varnish component, white wax from 2% to 6% by weight of a total weight of the second varnish component, and saccharin from 0.5% to 1.5% by weight of a total weight of the second varnish component.

Also, the first dental varnish component, the second dental varnish component, and a remainder of the amount of ethanol can be combined to produce a composition of a dental varnish. In some cases, the second dental varnish component can be cooled to a temperature from 50° C. to 80° C., from 55° C. to 75° C., or from 60° C. to 70° C. before being combined with the first dental varnish component. The first dental varnish component and the second dental varnish component can be mixed for a duration, such as 10 minutes to 40 minutes, from 12 minutes to 30 minutes, or from 15 minutes to 25 minutes. In some cases, a flavoring component can be added after the temperature of the mixture of the first dental varnish component and the second dental varnish component has cooled further to a temperature from 30° C. to 40° C., from 32° C. to 39° C. or from 34° C. to 38° C. Additionally, after the flavoring component has been added, mixing can take place for an additional duration, such as from 4 minutes to 20 minutes, from 6 minutes to 15 minutes, or from 8 minutes to 12 minutes.

The composition of dental varnish can include the first dental varnish component from 8% to 20% by weight of a total weight of the composition of dental varnish or from 10% to 16% by weight of a total weight of the composition of dental varnish. Additionally, the composition of dental varnish can include the second dental varnish component from 70% to 95% by weight of a total weight of the composition of dental varnish or from 80% to 90% by weight of a total weight of the composition of dental varnish. Further, the composition of dental varnish can include a flavoring component from 0.5% to 1.5% by weight of a total weight of the composition of dental varnish. Also, the composition of dental varnish can include a remainder of ethanol from 0.5% to 1.5% by weight of a total weight of the composition of dental varnish. In an illustrative example, the composition of dental varnish can include the first dental varnish component from 10% to 16% by weight of a total weight of the composition of the dental varnish, the second dental varnish component from 80% to 90% by weigh of a total weight of the composition of dental varnish, the flavoring component from 0.4% to 0.8% by weight of a total weight of the composition of dental varnish, and a remainder of the ethanol from 0.6% to 1.2% by weight of a total weight of the composition of dental varnish.

The compositions of dental varnishes described herein include ethyl cellulose at relatively low concentrations along with a colophonium/mastic based film forming component to effectively suspend a fluoride-containing source (e.g., sodium fluoride) in the dental varnishes. The use of the synthetic ethyl cellulose in place of naturally occurring tooth varnish suspending components (such as shellac and shellac wax), provides increased consistency of the dental varnish compositions, which in turn, can provide more effective treatment of dental problems. In particular, the fluoride source can be more uniformly distributed on the teeth that are contacted by the dental varnish compositions. Furthermore, the dental varnish compositions described herein minimize or eliminate phase separation and/or precipitation of the fluoride source. The film-forming properties of ethyl cellulose result in ease of application and retention to surfaces of teeth.

It is unexpected that the compositions of dental varnishes described herein provide rheological properties that achieve the substantially uniform suspension of a fluoride source without phase separation. In particular, the ethyl cellulose included in formulations described herein has viscosities that are less than those of previous compositions, which one of skill in the art would expect to cause a decrease in the viscosity of the overall dental varnish formulations. However, the lower viscosity ethyl cellulose included in the dental varnish formulations described herein provides a higher viscosity composition than previous dental varnish compositions. Thus, the rheological properties of the dental varnish formulations described herein are improved over the rheological properties of previous dental varnish formulations. The improved rheological properties result in a substantially uniform distribution of a fluoride source in the dental varnish formulations described herein, which causes the fluoride source to be more evenly distributed on the surface of teeth than previous dental varnish formulations. Accordingly, the effectiveness of the treatment and/or prevention of dental problems is also improved with respect to previous dental varnish formulations. In addition, the compositions of dental varnishes described herein can be thixotropic, and thus more easily spread during application. Such relatively high viscosity and thixotropic characteristics reduce and/or prevent the tendency of the compositions of dental varnishes described herein to run or drip upon application to tooth surfaces.

As will be evident to one of skill in the art, some components of the compositions of dental varnishes described herein may perform multiple functions, and the identification of a compound as having one function herein is not meant to exclude its use for other functions in a particular composition. Further, it is also understood that compounds in compositions of dental varnishes described herein may naturally react, disassociate, and/or form complexes with one another. Accordingly, certain components may be formed in situ, and also may in composition exist in different forms (for example, to the extent the sodium fluoride is dissolved, it will naturally disassociate into separate sodium and fluoride ions, as opposed to a solid salt). As is usual in the art, the compositions of the dental varnishes described herein are in terms of example composition components, without intending to exclude combinations of other components that result in the same or similar final compositions, or to exclude the natural reaction products of the described component combinations.

While the features of the disclosure have been described with reference to various embodiments, it will be understood by those skilled in the art that various modifications and variations may be made therein without departing from the scope of the features of the disclosure as defined by the appended claims

EXAMPLES

The following examples are further illustrative of the compositions of dental varnishes described herein, but it is understood that the compositions of dental varnishes are not limited thereto. All amounts and proportions referred to herein and in the appended claims are by weight, unless otherwise indicated.

Example 1—Phase Separation

The dynamic viscosity of compositions of dental varnishes was measured over a range of shear stresses. Table 1 shows the compositions tested. The commercial composition is a previous dental varnish composition that includes shellac. Composition 1 was a dental varnish composition that includes 3.00% of Aqualon®N-22 ethyl cellulose from Hercules Corp. Composition 2 was a dental varnish composition according to an embodiment described herein that includes 2.5% of Aqualon®N-50 ethyl cellulose from Hercules Corp. Composition 3 was a dental varnish composition according to an embodiment described herein that includes a 6.00% of Aqualon® N-10 ethyl cellulose from Hercules Corp. The viscosity was measured using a Brookfield viscometer having a v74 spindle at a shear rate of 1 rotation per minute (RPM). The majority of data points measured were between 10% torque and 100% torque. FitFlowYS software was used to calculate the viscosity with fitting parameters of n=0.5, rate range of 1 to 1000, yield stress in Pascals from 0.0001 to 1000 and high shear viscosity in Pascal seconds from 0.001 to 100. The yield stress was also measured using a Brookfield viscometer having a v74 spindle with a minimum shear rate of 0.5 RPM and a maximum shear rate of 200 RPM.

TABLE 1

Compositions of Dental Varnish Compositions

| Ingredient | Commercial Formula | Composition 1 | Composition 2 | Composition 3 |
|---|---|---|---|---|
| 96% ethanol | 27.21 | 27.66 | 28.16 | 24.66 |
| Colophonium-Compendial Grade | 32.31 | 32.83 | 32.83 | 32.83 |
| Sodium Fluoride-Micronized | 5.00 | 5.00 | 5.00 | 5.00 |
| Mastic-Compendial Grade | 11.94 | 27.18 | 27.18 | 27.18 |
| White Beeswax USP | 0.49 | 3.00 | 3.00 | 3.00 |
| Saccharin 550 | 0.69 | 0.69 | 0.69 | 0.69 |
| Wax-containing Shellac | 21.73 | — | — | — |
| Ethyl cellulose (22 cps) | — | 3.00 | — | — |
| Ethyl cellulose (10 cps) | — | — | — | 6.00 |
| Ethyl cellulose (50 cps) | — | — | 2.50 | — |
| Ethyl cellulose (100 cps) | | | | |
| Raspberry Flavor | 0.64 | 0.64 | 0.64 | 0.64 |
| Total Components | | | | |

TABLE 1-continued

Compositions of Dental Varnish Compositions

| Ingredient | Commercial Formula | Composition 1 | Composition 2 | Composition 3 |
|---|---|---|---|---|
| Viscosity (cps) | 400 | 3800 | 3200 | 5500 |
| Yield Stress-up (Pa) | 15 | 33 | 20 | 34 |
| Yield Stress-down (Pa) | 6.7 | 12.5 | 2.7 | 11.3 |
| Yield stress-ratio | 2 | 2 | 7 | 3 |
| Aesthetics | No Phase Separation | No Phase Separation | No Phase Separation | No Phase Separation |

The compositions of Table 1 were tested for phase separation using an analytical centrifuge. The process used to test the compositions of Table 1 were conducted according to the following parameters: 255 data points collected, 600 second intervals, speed of 500 rotations per minute (rpm), a temperature of 30° C., and for a duration of 42 hours. Phase separation did not occur for Compositions 1-3, but there was some minor phase separation for composition 4.

Example 2—Retention on Enamel Surface

Samples of bovine enamel were coated with Composition 1, Composition 2, Composition 3, and the Commercial Formula specified in Table 1. The samples were tested for retention of the compositions on the enamel surfaces. In particular, an even coat of varnish was applied to the samples and then the samples were weighed. Each sample was then placed in a container including artificial saliva in an incubator with constant shaking of the container. After one hour, the samples were removed from the containers, dried, and weighed. The samples were placed in fresh artificial saliva, removed from the containers after 4 hours total, dried and then re-weighed after 4 hours. The process was repeated for 24 hours. Table 2 shows average values and standard deviation for varnish retention on bovine enamel for dental varnish compositions at different times. The varnish retention of the ethyl cellulose containing Compositions 1-3 was improved over the varnish retention of the Commercial Formula.

TABLE 2

| | % Retention after 1 hour | Standard Deviation | % Retention after 4 hour | Standard Deviation | % Retention after 24 hour | Standard Deviation |
|---|---|---|---|---|---|---|
| Composition 1 | 94.4 | 2.7 | 73.4 | 1.4 | 63.7 | 6.9 |
| Composition 2 | 86.6 | 5.4 | 70.4 | 3.3 | 59.8 | 13.8 |
| Composition 3 | 63.4 | 12.2 | 55.9 | 11.9 | 46.1 | 4.4 |
| Commercial Formula | 74.5 | 30.68 | 65.6 | 39.62 | 51.1 | 37.13 |

Example 3—Fluoride Release

Fluoride release for Composition 1, Composition 2, Composition 3, and the Commercial Formula of Table 1 was measured per gram of varnish applied to an enamel surface. The fluoride release was measured by cutting bovine enamel specimens and preparing the specimens to fit on the end of ¼ inch Plexiglas rods. The dimensions of the specimens were 6×6 mm². The edges of the specimens were covered with nail varnish so that only enamel was exposed. The rods with specimens were identified with a unique specimen number and placed on an analytical balance (0.0001 g). The balance was tarred and the exposed enamel surfaces were coated with the test material in the manner described in the instructions from the manufacturer and allowed to cure. This resulted in uniform sized samples of the varnishes having dimensions of 36 mm² with a measured mass of varnish on the surface. Six specimens of each composition of Table 1 were prepared. The specimens were individually placed into 2.0 ml of deionized water with constant stirring of 130 rpm. After 5, 15, 30 minutes and 1, 4 and 24 hours the specimens were removed from their water samples and placed in fresh deionized water. At the end of the 24 hours, the water samples were analyzed for fluoride content by adding 2.0 ml of TISAB and comparing the my potential readings obtained to the readings obtained from a standard curve prepared at the same time and in a similar fashion. A combination fluoride electrode and a digital my meter were used.

The cumulative amounts of fluoride released in mg per gram of dental varnish are shown for Composition 1, Composition 2, Composition 3 and the Commercial Formula in Table 3.

TABLE 3

Fluoride Release in milligrams per gram of Varnish Applied

| Time of Measurement | Composition 1 | Composition 2 | Composition 3 | Commercial Formula |
|---|---|---|---|---|
| 5 minutes | 0.23 | 0.33 | 0.25 | 0.23 |
| 15 minutes | 0.26 | 0.37 | 0.30 | 0.26 |
| 30 minutes | 0.29 | 0.40 | 0.33 | 0.29 |

TABLE 3-continued

Fluoride Release in milligrams per gram of Varnish Applied

| Time of Measurement | Composition 1 | Composition 2 | Composition 3 | Commercial Formula |
|---|---|---|---|---|
| 1 hour | 0.34 | 0.46 | 0.38 | 0.35 |
| 4 hours | 0.46 | 0.58 | 0.51 | 0.57 |
| 24 hours | 0.69 | 0.74 | 1.06 | 1.06 |

Example 4—Fluoride Uptake

Fluoride uptake on sound enamel and on lesioned enamel was also measured for compositions of Table 1. The fluoride uptake was measured in parts per million. Table 4 shows fluoride uptake on sound enamel for Composition 1, Composition 2, Composition 3, and the Commercial Formula of dental varnishes shown in Table 1 and Table 5 shows fluoride uptake on lesioned enamel for Composition 1, Composition 2, Composition 3, and the Commercial Formula of dental varnishes shown in Table 1. The mean fluoride uptake for Compositions 1-3 including ethyl cellulose was comparable to that of the shellac-containing Commercial Formula. The fluoride uptake was measured according to Procedure 40 in the FDA Monograph except that sound enamel is used in addition to incipient lesioned enamel.

TABLE 4

Fluoride Uptake for Sound Enamel

| | Mean Fluoride Uptake (ppm) | Standard Deviation |
|---|---|---|
| Composition 1 | 3015.05 | 591.1 |
| Composition 2 | 3285.55 | 803.92 |
| Composition 3 | 3440.42 | 842.75 |
| Commercial Formula | 3508.14 | 881.64 |

TABLE 5

Fluoride Uptake for Lesioned Enamel

| | Mean Fluoride Uptake (ppm) | Standard Deviation |
|---|---|---|
| Composition 1 | 756.76 | 97.26 |
| Composition 2 | 311.53 | 74.45 |
| Composition 3 | 385.36 | 85.35 |
| Commercial Formula | 402.74 | 135.19 |

Example 5—Varnish Appearance

An amount of the dental varnish composition of the commercial formula was applied to a first portion of a synthetic tooth surface and an amount of an ethyl cellulose containing dental varnish composition number 2 of Table 1 was applied to a second portion of a synthetic tooth surface. The portions of the synthetic tooth surface that were treated with the commercial formula dental varnish composition exhibited a yellowish tint. In contrast, the portions of the synthetic tooth surface that were treated with the ethyl cellulose containing dental varnish composition were clear and not tinted. Thus, the ethyl cellulose containing dental varnishes provide an improved appearance over the shellac-containing commercial formula of Table 1.

What is claimed is:

1. A dental varnish composition comprising:
a fluoride source;
a non-aqueous solvent:
ethyl cellulose in an amount effective to achieve suspension of the fluoride source, and
one or more resins selected from mastic, colophonium, or a combination thereof; wherein a high shear viscosity of the dental varnish composition is from 1,500 centipoise (cps) to 6,500 centipoise (cps) and wherein the ethyl cellulose has a viscosity no greater than 45 centipoise (cps).

2. The dental varnish composition of claim 1, wherein the one or more resins include colophonium present in an amount from 28% to 38% and mastic present in an amount from 22% to 32%.

3. The dental varnish composition of claim 1, wherein the ethyl cellulose is present in an amount from 1% to 10%.

4. The dental varnish composition of claim 1, wherein the fluoride source is sodium fluoride and the fluoride source is present in an amount from 2% to 8%.

5. The dental varnish composition of claim 1, wherein the dental varnish composition has a ratio of yield stress as a shear rate is ramping up to yield stress when a shear rate is ramping down from 2.5 and 5.0.

6. The dental varnish composition of claim 1, wherein:
the fluoride source is present in an amount from 4% to 6%,
the non-aqueous solvent is ethanol present in an amount from 24% to 30%;
ethyl cellulose is present in an amount from 1% to 10%;
mastic is present in an amount from 26% to 30%; and
colophonium is present in an amount from 29% to 35%.

7. The dental varnish of claim 6, wherein the ethyl cellulose has a viscosity from 7 cps to 12 cps and is present in an amount of 3% to 8%.

8. The dental varnish of claim 6, wherein the ethyl cellulose has a viscosity from 17 cps to 25 cps and is present in an amount of 1% to 5%.

9. The dental varnish composition of claim 1, further comprising beeswax present in an amount of 1% to 6%, a sweetener component present in an amount of 0.4% to 0.9%; and a flavoring component present in an amount of 0.4% to 0.9%.

10. The dental varnish composition of claim 1, wherein the dental varnish composition is free of shellac.

11. The dental varnish composition of claim 1, wherein a high shear viscosity of the dental varnish composition is from 3,500 cps to 5,800 cps.

12. The dental varnish composition of claim 1, wherein a total amount of the one or more resins is from 42% to 70%.

13. The dental varnish composition of claim 1, wherein the ethyl cellulose has a viscosity from 8 cps to 11 cps and is present in an amount from 5% to 7% or the ethyl cellulose has a viscosity from 18 cps to 24 cps and is present in an amount from 2% to 4%.

\* \* \* \* \*